(12) United States Patent
Cettina et al.

(10) Patent No.: US 8,308,675 B2
(45) Date of Patent: Nov. 13, 2012

(54) APPLICATOR DEVICE

(75) Inventors: Melinda Cettina, Robbinsville, NJ (US); Paul Y. Fung, South River, NJ (US); Gina Marcus, Trenton, NJ (US); Hans-Werner Schoelling, Ennepetal (DE); Jennifer Sturgeon, Long Valley, NJ (US); Alan G. Trojanowski, Monmouth Junction, NJ (US); Simone Weitz, Dortmund (DE)

(73) Assignee: McNeil-PPC, Inc., Skillman, NJ (US)

( * ) Notice: Subject to any disclaimer, the term of this patent is extended or adjusted under 35 U.S.C. 154(b) by 545 days.

(21) Appl. No.: 11/693,388

(22) Filed: Mar. 29, 2007

(65) Prior Publication Data

US 2008/0243046 A1    Oct. 2, 2008

Related U.S. Application Data

(60) Provisional application No. 60/788,361, filed on Mar. 31, 2006.

(51) Int. Cl.
*A61F 13/20* (2006.01)

(52) U.S. Cl. .......................................... 604/15; 604/904

(58) Field of Classification Search .................... 604/11, 604/13, 14, 15, 16, 17, 18, 385.17, 385.18, 604/904

See application file for complete search history.

(56) References Cited

U.S. PATENT DOCUMENTS

| | | | |
|---|---|---|---|
| 2,330,257 A | 9/1943 | Bailey | |
| 2,587,717 A | 3/1952 | Fourness | |
| 2,687,717 A | 3/1952 | Fourness | |
| 3,347,234 A | 10/1967 | Voss | |
| 3,699,962 A | 10/1972 | Hanke | |
| 4,291,696 A * | 9/1981 | Ring | 604/14 |
| 4,536,178 A * | 8/1985 | Lichstein et al. | 604/15 |
| 4,573,964 A * | 3/1986 | Huffman | 604/15 |
| 4,921,474 A | 5/1990 | Suzuki | |
| 5,080,659 A | 1/1992 | Nakanishi | |
| 5,090,962 A | 2/1992 | Landry, Jr. et al. | |
| 5,127,906 A | 7/1992 | Landry, Jr. et al. | |
| 5,350,371 A | 9/1994 | Van Iten | |
| 5,533,966 A * | 7/1996 | Schoelling | 604/18 |
| 5,643,196 A * | 7/1997 | Child et al. | 604/14 |
| 5,788,663 A * | 8/1998 | Igaue et al. | 604/15 |
| 5,910,520 A | 6/1999 | Dabi et al. | |
| 5,958,321 A * | 9/1999 | Schoelling et al. | 264/318 |

(Continued)

FOREIGN PATENT DOCUMENTS

BE    800 938 A2    10/1973

(Continued)

OTHER PUBLICATIONS

A. Hunting, "encyclopedia of shampoo ingredients" 1985, Michelle Press, US 146860, XP002332078, p. 296-297.

*Primary Examiner* — Nicholas Lucchesi
*Assistant Examiner* — Benedict L Hanrahan

(57) ABSTRACT

An applicator device capable of housing an insertable element includes a plunger member that is slideably engaged with the insertion member and has an insertion end and a gripper end. The gripper end of the plunger member consists of a locking mechanism having a diameter greater than the diameter of the plunger member. The insertion member also includes a locking mechanism that is capable of engaging the locking mechanism of the plunger member that may prevent the plunger member from withdrawal.

10 Claims, 12 Drawing Sheets

U.S. PATENT DOCUMENTS

| | | | |
|---|---|---|---|
| 5,972,322 A | 10/1999 | Rath | |
| 6,165,453 A | 12/2000 | Buheitel | |
| 6,171,426 B1 | 1/2001 | Blanchard | |
| 6,306,906 B1 | 10/2001 | Wohlman | |
| 6,423,025 B1 * | 7/2002 | Buzot | 604/15 |
| 6,432,076 B1 | 8/2002 | Wada | |
| 6,450,986 B1 * | 9/2002 | Binner et al. | 604/15 |
| 6,890,324 B1 | 5/2005 | Jackson | |
| 6,936,211 B2 * | 8/2005 | Binner et al. | 264/295 |
| 2002/0160023 A1 | 10/2002 | Bagdi | |
| 2003/0086897 A1 | 5/2003 | Ohta | |
| 2004/0064082 A1 | 4/2004 | LeMay | |
| 2004/0199100 A1 | 10/2004 | LeMay | |
| 2004/0199102 A1 | 10/2004 | LeMay | |
| 2004/0243088 A1 | 12/2004 | LeMay | |
| 2005/0070839 A1 | 3/2005 | Jackson | |
| 2005/0256483 A1 * | 11/2005 | Przepasniak et al. | 604/385.17 |
| 2006/0111662 A1 * | 5/2006 | Karapasha et al. | 604/16 |
| 2006/0217652 A1 * | 9/2006 | Heuer et al. | 604/15 |
| 2008/0033337 A1 * | 2/2008 | Dougherty et al. | 604/15 |
| 2010/0204636 A1 * | 8/2010 | Lemay et al. | 604/15 |

FOREIGN PATENT DOCUMENTS

| | | |
|---|---|---|
| DE | 20213416 | 12/2002 |
| EP | 1695 680 B | 8/2006 |
| WO | WO 01/19328 A | 3/2001 |
| WO | WO 03/002048 A | 1/2003 |
| WO | WO 2006/055794 A | 5/2006 |

* cited by examiner

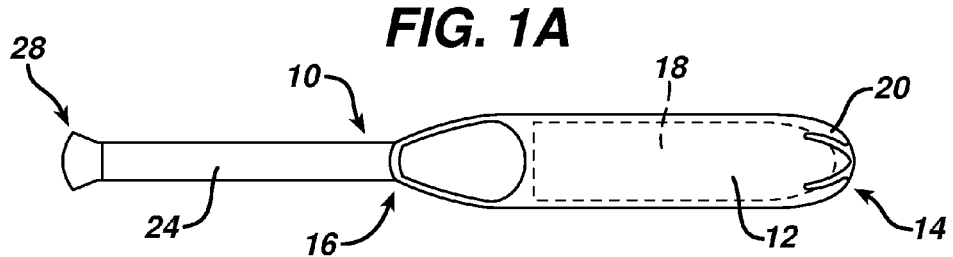
FIG. 1A
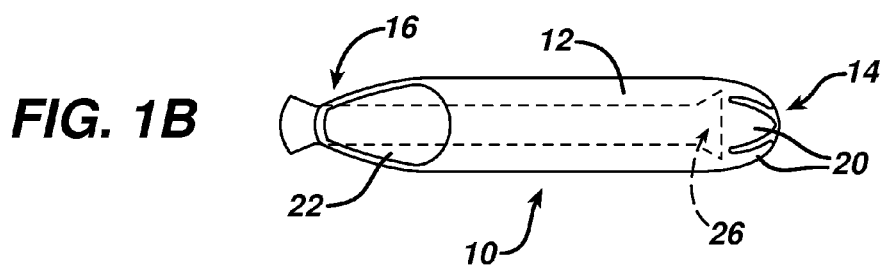
FIG. 1B
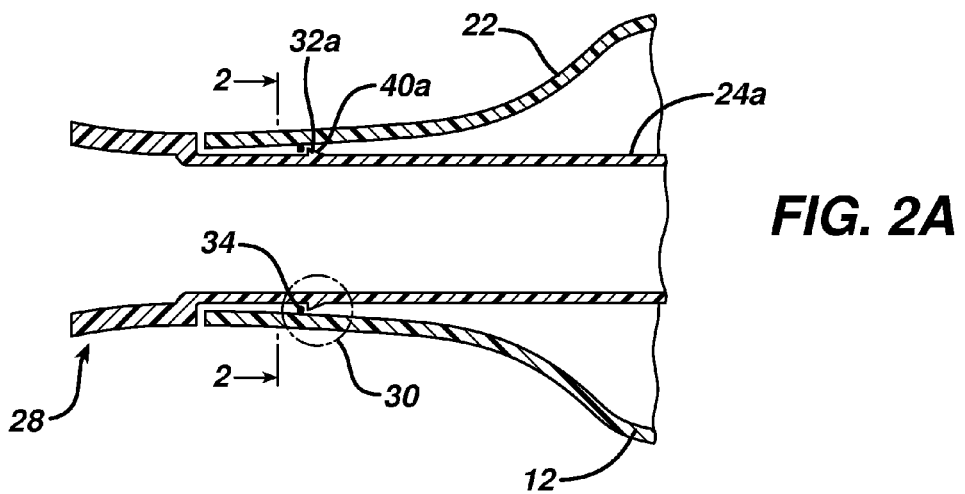
FIG. 2A
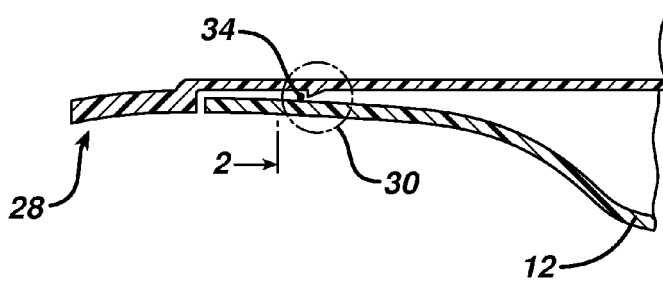
FIG. 2B
FIG. 2C

APPLICATOR DEVICE

CROSS-REFERENCE TO RELATED APPLICATIONS

This application claims the benefit of U.S. provisional application 60/788,361 filed on Mar. 31, 2006, the complete disclosure of which is hereby incorporated herein by reference for all purposes.

FIELD OF THE INVENTION

The present invention generally relates to applicators that have a locking/snap-in mechanism and that are capable of housing an insertable element and in particular a tampon applicator that provides the user with a tactile perceptual cue, indicating that the insertable element is appropriately deployed, e.g., fully expelled.

BACKGROUND OF THE INVENTION

Applicators, as known in the art, are used to house objects intended to be inserted in a body cavity, such as a tampon and to expel the objects into the intended orifice. Typically, applicators comprise an insertion member and a plunger. The object to be expelled from the applicator, such as a tampon, is positioned within the insertion member. The insertion member has a first end for insertion of the tampon and a second end for receipt of the plunger. To use the applicator, the user will position the first end appropriately, grasp the insertion member, and push the plunger into the insertion member towards the first end to insert the tampon. A variety of applicators have employed visual marks to determine when the contents of the applicator have been fully expelled.

Various locking mechanism configurations have been proposed to facilitate the handling of the applicator and to improve insertion thereof. One approach is a tampon applicator as disclosed in U.S. Pat. No. 2,587,717, with a locking mechanism comprising of a locking ear punched inwardly in the barrel and a plunger having a locking ear that points inwardly into the interior of the plunger. Locking occurs when the both ears are engaged with each other and the plunger is prevented from removal due to the locking ear of the barrel catching an open area created by the locking ear of the plunger. Another approach is a tampon applicator as disclosed in U.S. Pat. No. 3,347,234 comprising an applicator provided with means to stabilize the position of the inner tube with the outer tube. The stabilizer means may be in the form of small detent or flaps extending downwardly and forwardly form the outer tube. The detents inhibit rearward withdrawal of the inner tube from the outer tube, but do not inhibit the forward movement or the inner tuber relative the outer tube.

Where as these designs have functioned well for their intended purposes, there still remains a need for a tampon applicator having an improved locking mechanism. Accordingly, it is believed that the design of the present invention will provide an applicator with an improved locking mechanism comprised of an insertion member, a plunger member, and compatible locking mechanisms for each member that will improve the user's insertion experience as well as provide the user with a visual cue upon locking.

The citation of any document herein is not to be construed as an admission that it is prior art with respect to the present invention.

SUMMARY OF THE INVENTION

An applicator device capable of housing an insertable element has an insertion member having an insertion end and an opposed gripper end, a plunger insertable into the gripper end of the insertion member and having an insertion end and an opposed gripper end, and a locking mechanism comprising at least one plunger lock element and at least one insertion member lock element. The plunger is slidable in the insertion member between a first position, substantially contained within the insertion member with the plunger insertion end disposed toward the insertion member insertion end, and a second position, substantially withdrawn from the insertion member. The at least one plunger lock element and the at least one insertion member lock element are capable of engaging when the plunger is disposed in the first position. In one embodiment, the at least one plunger lock element is spaced apart from the gripper end of the plunger, and the at least one insertion member lock element is spaced apart from the gripper end of the insertion member. In another embodiment, the at least one plunger lock element is disposed proximate the gripper end of the plunger, and the at least one insertion member lock element is disposed proximate the gripper end of the insertion member.

A method of inserting an element into a body cavity includes the steps of inserting into the body cavity an applicator, sliding the plunger of the applicator into the insertion member, expelling an insertable device from the insertion end of the applicator and into the body cavity, and withdrawing the applicator from the body cavity by withdrawing its plunger. The applicator includes an insertion member having an insertion end and an opposed gripper end, a plunger insertable into the gripper end of the insertion member and having an insertion end and an opposed gripper end, and a locking mechanism. The locking mechanism includes at least one plunger lock element and at least one insertion member lock element. The at least one plunger lock element engages the at least one insertion member lock element. Again, the plunger is slidable in the insertion member between a first position, substantially contained within the insertion member with the plunger insertion end disposed toward the insertion member insertion end, and a second position, substantially withdrawn from the insertion member. Preferably, the detection of the engagement of the at least one plunger lock element and the at least one insertion member lock element permits the user to determine appropriate deployment of the insertable device in the body cavity. The engagement of the at least one plunger lock element and the at least one insertion member lock element remain continues during the withdrawal of the plunger to remove also the insertion member.

BRIEF DESCRIPTION OF THE DRAWINGS

Examples of embodiments of the present invention will now be described with reference to the drawings, in which:

FIG. 1A is a side elevation of an applicator according to the present invention comprising a tubular insertion member and a plunger member disposed therein;

FIG. 1B is a partial side elevation of the applicator of FIG. 1A after complete insertion of the plunger member into the insertion member;

FIG. 2A is a longitudinal section of a device according to FIG. 1;

FIGS. 2B and 2C are cross sections of the device along line 2-2 of FIG. 2A;

DETAILED DESCRIPTION OF THE INVENTION

Figure 3:
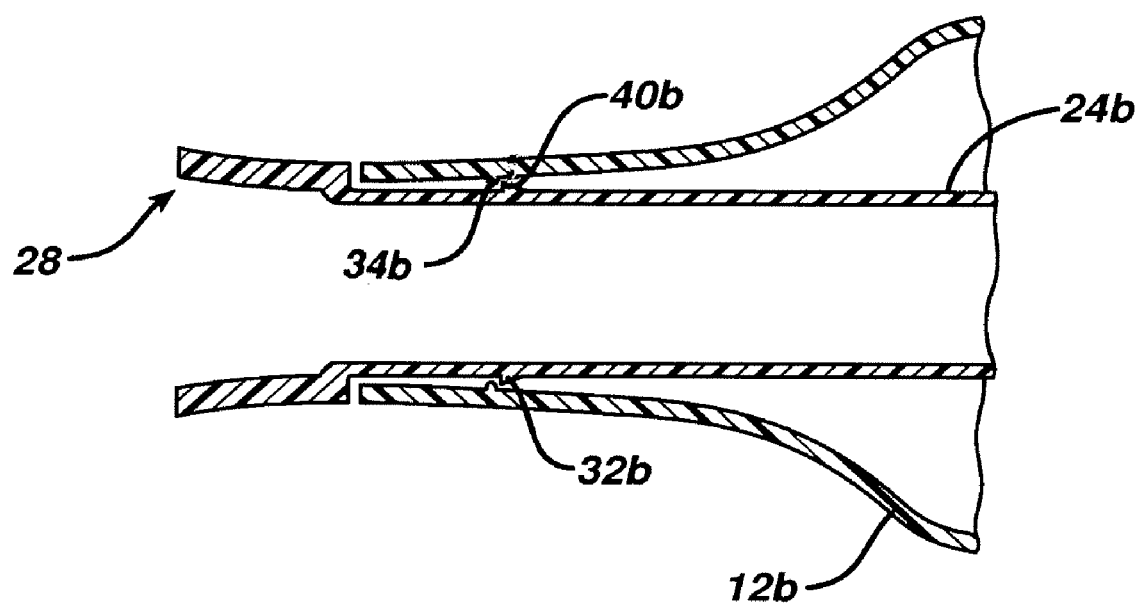
FIGS. 3-5 are partial longitudinal sections of alternative embodiments of the present invention.

As used herein the specification and claims, the term "applicator" refers to a mechanism or implement that facilitates the insertion of a tampon or other structure into an external orifice of a mammal. The term includes, without limitation, any known hygienically designed applicator that is capable of receiving a tampon and may be used for insertion of a tampon, including the telescoping, tube and plunger and the compact applicators, an applicator for providing medicament to an area for prophylaxis or treatment of disease, a spectroscope containing a microcamera in the tip connected via fiber optics, a speculum of any design, a tongue depressor, a tube for examining the ear canal, a narrow hollow pipe for guiding surgical instruments, and the like.

As used herein the specification and claims, the term "tampon," refers to any type of absorbent structure that is inserted into the vaginal canal or other body cavities for the absorption of fluid therefrom, to aid in wound healing, or for the delivery of active materials, such as medicaments, or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis, and a radial axis. The tampon's length can be measured from the insertion end to the withdrawal end along the longitudinal axis.

As used herein the specification and the claims, the term "rigidity" and related terms mean the longitudinal stability of the device. Normally specified as the unit for rigidity is the force that is necessary to compress the element in the longitudinal direction by a specific length (N/cm).

As used in the specification and claims, the term "aperture" and variants thereof, mean an opening in the surface of the tubular insertion device which forms a discontinuity in the tube-forming material at the edges of the opening, at least at the leading and trailing edges thereof. This aperture thereby provides relatively abrupt, finger-accepting edges to frictionally resist movement of a user's finger in response to longitudinal forces on the device.

While the present invention generally relates to applicator devices having a tubular insertion member, the following detailed description will refer, specifically, to a locking tampon applicator for ease of understanding. One of ordinary skill in the art will recognize other uses for this invention including, without limitation, applicators for other intravaginal devices, such as collection cups, inflatable plugs or cups, and the like; incontinence devices; suppositories; nasal packing; and the like.

The present invention relates to applicators for delivering materials into body cavities, comprising an elongate insertion member and a plunger member having locking mechanisms for at least partial insertion into a body cavity. The elongate insertion member has an insertion end and gripper end opposite thereof. The plunger member has an insertion end and gripper end opposite thereof.

Referring now to the drawings, wherein like reference numerals designate like elements, FIG. 1 depicts an applicator 10, comprising a tubular insertion member 12, having a cylindrical central portion, an insertion end 14 and a gripper end 16, that is suitable to contain an insertable device 18 for the body cavity. The insertion end 14 may have a plurality of petals 20 that curve inwardly from the cylindrical central portion to form a substantially closed insertion end, and the gripper end 16 may have a structure 22 of smaller diameter than the cylindrical central portion of the tubular insertion member to enhance the user's grip on the applicator. The applicator 10 also includes a plunger member 24 having an insertion end 26 that is insertable into the smaller diameter of the gripper end of the tubular insertion member 12 and is capable of bearing against the device 18. The plunger member 24 terminates in a gripper end 28, opposite the insertion end 26, that may be manipulated to move the insertion end 26 within the tubular insertion member 12. The insertion end 26 of the plunger member 24 is arranged and configured for slidable introduction into the tubular insertion member 12 through the smaller diameter portion of its gripper end 16. As shown, e.g., in FIG. 2A, the outer surface of the gripper end 28 of the plunger member 24 and the outer surface of the structure 22 at the gripper end 16 of the tubular insertion member 12 are aligned adjacent to one another to form a substantially continuous finger grip area when the plunger member 24 is fully inserted into the tubular insertion member 12.

The applicators 10 or other tubular devices of the present invention can have tube geometries or cross-sections that are useful to contain the object to be inserted. Often, the shape of the insertable device 18 contained suggests the shape of the tubular insertion member 12, but departures from this general rule may be made. Therefore, the tubular insertion member 12 may take on numerous cross-sectional shapes including, without limitation, circular, oval, polygonal (e.g., trapezoidal, rectangular, triangular), and the like. For example, cylindrical tampons may be contained within rectangular insertion members and trapezoidal tampons (such as those disclosed in Van Iten et al., U.S. Pat. No. 5,350,371) and cup-shaped tampons (such as those disclosed in Bailey, U.S. Pat. No. 2,330,257) can be contained in a generally cylindrical insertion member. In addition, the insertion member 12 can substantially elongated, curved, or flexible, or it can take on other shapes that are apparent to one of ordinary skill in the art. The specific geometry, itself, is not critical to the practice of the present invention. In addition, the edge of the tubular device (both finished and unfinished) may be a standard, planar edge coincident with a plane perpendicular to the longitudinal axis of the tubular device.

The applicator devices of the present invention can be made of materials known to those of ordinary skill in the art. Generally, the applicators may be plastic or paper. Plastic materials include, without limitation, polyolefins such as polyethylene and polypropylene, polyesters such as polyethylene terephthalate, polycaprolactone, polyvinyl alcohol, ethylene-vinyl acetate copolymers, cellophane, PHBV such as those disclosed in Dabi et al., U.S. Pat. No. 5,910,520 (herein incorporated by reference), starch-based polymers including those disclosed in Dabi et al., U.S. Pat. No. 5,910,520, and the like. The expulsion member can be formed as a solid or a tubular element.

Paper materials include, without limitation, paperboard, cardboard, cup stock, paper, and the like. The paper may be a single layer of material, or it can be a plurality of laminated layers to provide multiple benefits relating to the various layers. Laminated paper material may include a surface layer or coating of plastic, wax, silicone, lubricants, and the like, which may be useful to increase the comfort to the user during insertion and withdrawal. The plastic coating may include, without limitation, those plastic materials listed above. Laminated paper material may also include additional layers such as adhesive layers, tie layers, and the like.

An example of such a surface layer is disclosed in Blanchard, U.S. Pat. No. 6,171,426. A representative, non-limiting list of useful materials to be used as the surface layer includes, waxes, cellophane, polyolefins, polyesters, epoxies, and the like. The surface layers may also include thermal stabilizers, pigments, fragrances, surfactants, antimicrobial agents, medicaments, and the like.

Typical dimensions for each of the tubular insertion and plunger members include a length of from about 50 to about 100 millimeters, a diameter of from about 8 to about 16 millimeters, and a thickness of from about 0.4 to about 0.6 millimeters. Preferably, the diameter of the plunger member is less than the diameter of the tubular insertion member to allow for a telescopic arrangement of the two.

The tubular insertion member of the applicator provided by the present invention is preferably substantially closed prior to expulsion of the materials contained therein. Alternatively, the insertion end of the applicator can be more or less open, that is the diameter along the length of the tubular insertion member is substantially equivalent to the diameter of the insertion end. Procter & Gamble, of Cincinnati, Ohio, currently offers for sale an open-ended tampon applicator under the trade name TAMPAX® flushable applicator tampons.

In order to facilitate insertion and removal of the applicator 10 from the body, we have provided a locking mechanism 30 to secure together the insertion member and the plunger for removal. This mechanism includes at least one plunger lock element 32 and at least one insertion member lock element 34. Each of these lock elements may be spaced away from the gripper end of their respective members, e.g., the at least one plunger lock element 34 may be located in a central portion of the plunger 24 or even proximate the insertion end 26 of the plunger 24. Alternately, a preferred embodiment positions the at least one plunger lock element 32 proximate the gripper end 28 of the plunger 24. Such arrangement would engage at least one insertion member lock element 34 proximate the gripper end 16 of the insertion member 12.

Useful locking mechanisms may include any one or more of the following:

A system (FIG. 2) in which the plunger member 24a has a raised ring 32a on its outside diameter near the finger grip end 28 with a taper lead 40a that can move beyond at least one resilient element, e.g., an elastic member or spring wire forming a chord within the interior of the insertion member. In more detail, FIG. 2B shows an insertion member 12a with a locking mechanism 34a in a relaxed position without the plunger member 24a. FIG. 2C shows an engaged locking mechanism of this type with insertion member locking mechanism 34a in an elongated positions distorted by the plunger member 24a after passage of plunger member locking mechanism 32a.

A system (FIG. 3) in which the plunger member 24b has a raised ring 32b on its outside diameter near the finger grip end 28 with a taper lead 40b that can move beyond at least one internal raised ring 34b on the inside surface of the insertion member 12b. The interference of the internal and external raised sections holds the plunger member 24b and the insertion member 12b together. Of course, the raised ring with a taper lead may be disposed on an interior surface of the insertion member with a corresponding ring on an outer surface of the plunger.

A detent system may also be used.

Figure 4:
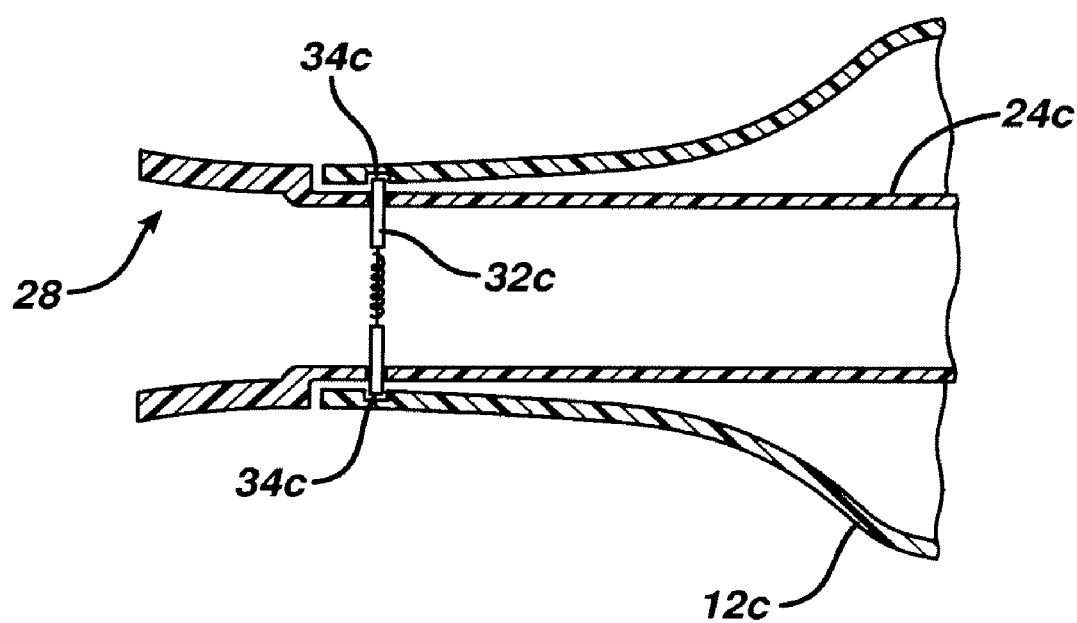

In one example shown in FIG. 4, the plunger member 24c has raised, spring-loaded detent element 32c extending beyond its outside diameter near the finger grip end 28, and the insertion member 12c has a mating groove or gap 34c on its inner surface to accommodate the detent element 32c. The interference of the spring-loaded detent element 32c and the groove 34c holds the plunger member 24c and the insertion member 12c together.

Figure 5:
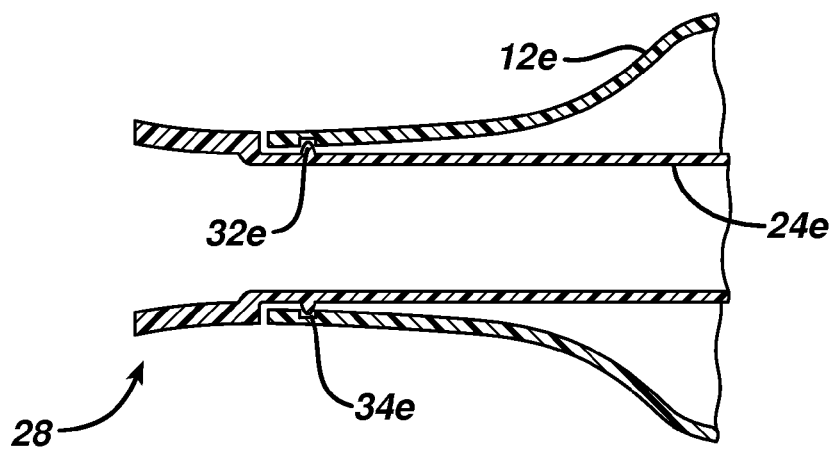
Figure 6A:
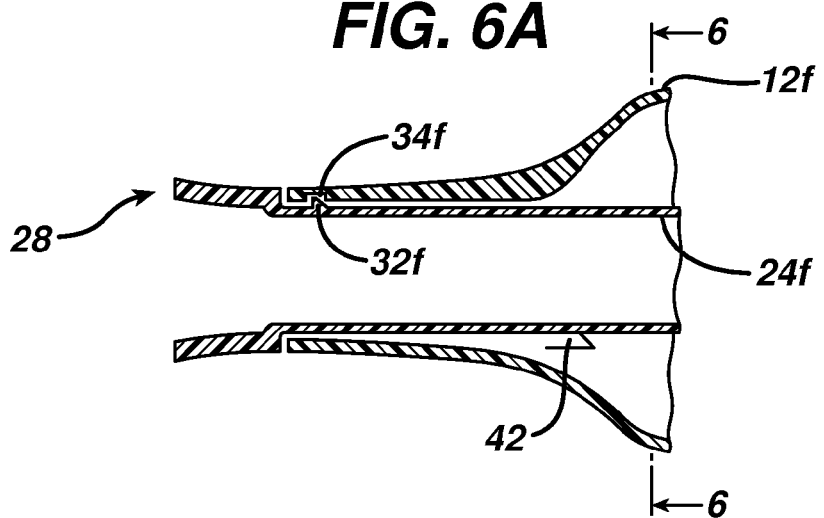
FIG. 6A is a longitudinal section of an alternative embodiment of the present invention.
Figure 6B:
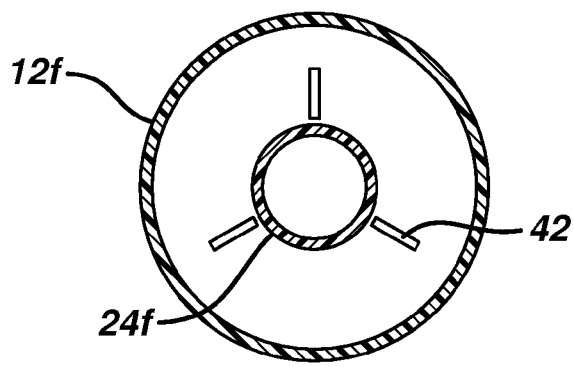
FIG. 6B is a cross section of the device along line 6-6 of FIG. 6A.

In other examples shown in FIGS. 5 and 6, the plunger member 24 has one or more protrusion 32e,32f in the form of a ring or point on its outer surface near the gripper end 28. When assembled the protrusion(s) 32e,32f is capable of interlocking with a corresponding groove 34e,34f in the inner surface of the insertion member 12 to hold the insertion member 12 and plunger member 24 together for withdrawal. Such an arrangement may provide the opportunity to orient an insertable device 18 within the applicator and deliver it to the body cavity in a desired orientation. In this embodiment shown in FIG. 6A, a raised point 32f may be rotated to be aligned with a mating depression or void 34f on the inner surface of the insertion member 12. One or more of these raised features may have a taper lead surface, e.g., leading surface 40f of the protrusion 32f that will initially contact the other element of the interlocking structure to help guide the elements past each other. FIG. 6B shows a cross-section along line B-B of FIG. 6A with a view toward the gripper end 16 of the insertion member 12. This view shows a plurality of fins 42 extending from the inner surface of the insertion member 12 to stabilize the plunger member 24 within the insertion member 12.

Figure 7A:
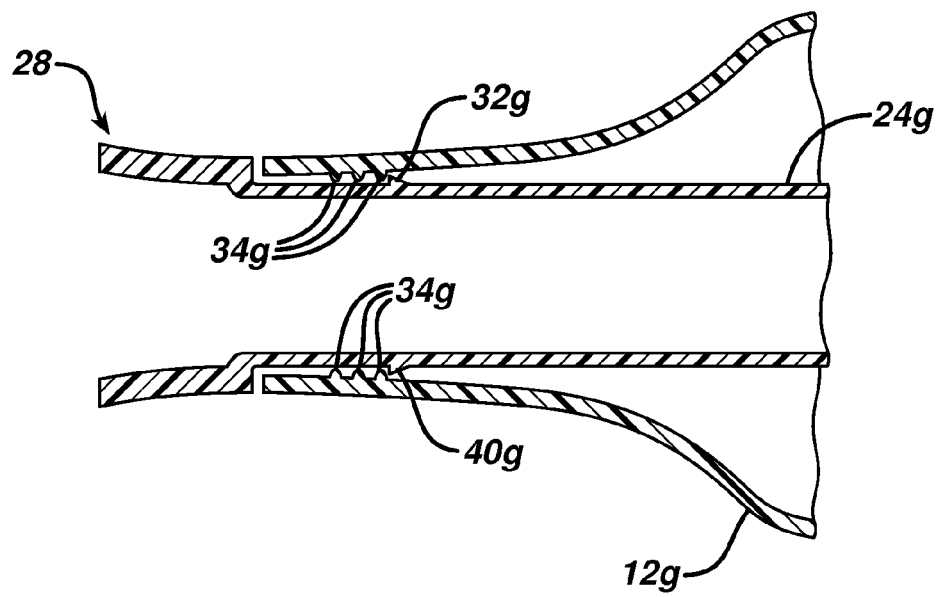
FIGS. 7A-9 are partial longitudinal sections of alternative embodiments of the present invention.
Figure 7B:
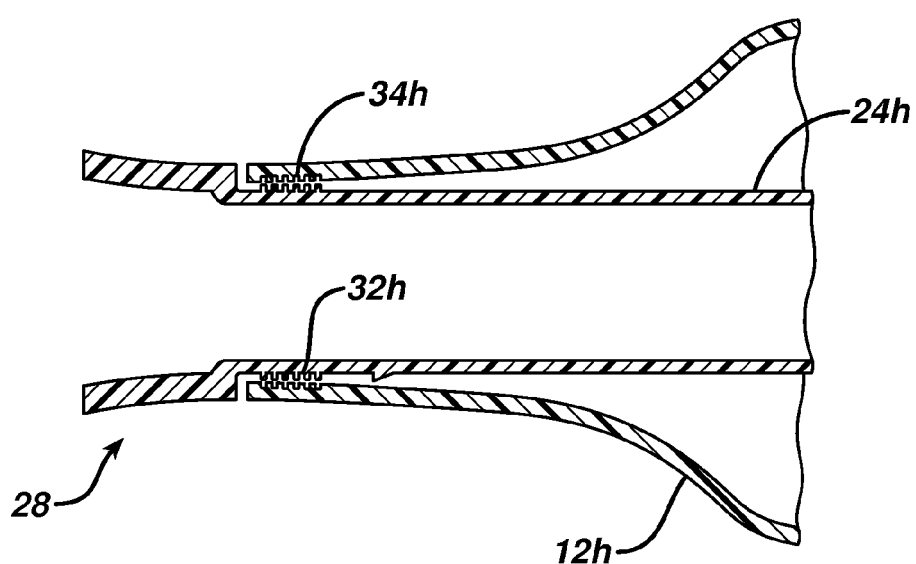
Figure 7C:
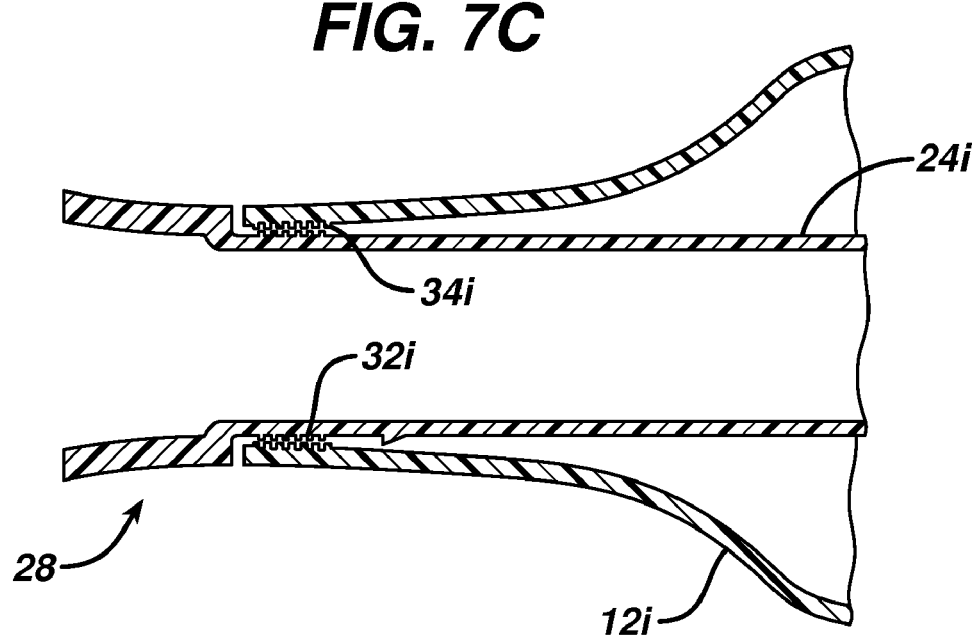

A similar system shown, e.g., in FIGS. 7A-7C, incorporates one or more raised elements on both the insertion member 12 and plunger member 24. In particular, a plunger member 24g may have a raised ring 32g on its outer surface near the gripper end 28 with a tapered lead 40g to move into and beyond a plurality of internal raised ribs 34g on the inner surface of the insertion member 12g as shown in FIG. 7A. Alternatively, the plunger member 24h has a plurality of raised rings 32h on its outer surface, and the insertion member 12h has a plurality of circumferential grooves 34h as shown in FIG. 7B. In another variation shown in FIG. 7C, the insertion member grooves 34h may be replaced with a plurality of raised rings 34i to interact with the plunger member rings 34*i*, as described above (the raised rings of one element would generally be stable in the gaps between the rings of the interlocking element. Axial orientation is not necessary for proper function of these embodiments.

While the foregoing have described an element on either the plunger or the barrel, one of ordinary skill in the art will readily recognize that the individual interlocking elements may be switched from the plunger to the barrel and vice versa.

Figure 8:
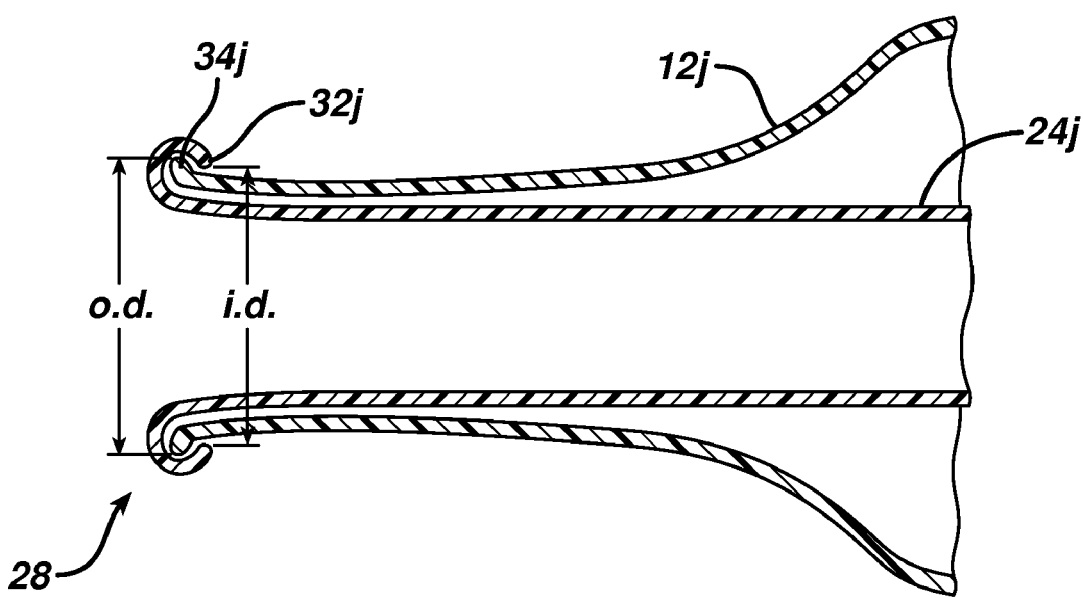

A resilient outer lip system (FIG. 8) employs a plunger member 24*j* having an outer diameter at its gripper end 28 that is larger than that of the gripper end 16 of the insertion member 12*j*. However, the outer lip 32*j* of the plunger member gripper end 28 has in inner diameter less than the outer diameter of the insertion member gripper end 16. Therefore, the plunger member outer lip 32*j* is stretched over the insertion member gripper end 16, and the outer lip 32*j* engages the outer rim 34*j* of the insertion member 12*j* to hold the plunger member 24*j* and the insertion member 12*j* together.

Figure 9:
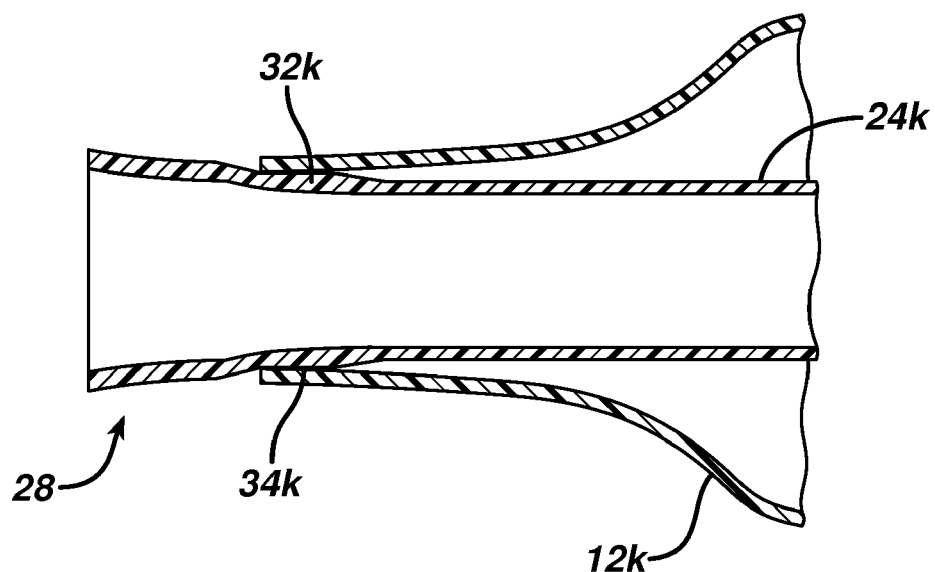

An interference fit system (FIG. 9) may use a plunger member 24 having a tapered shaft portion 32*k* to increase the outside diameter of the plunger member 24*k* as it approaches the plunger member gripper end 28. When the plunger member 24*k* is pushed into the insertion member 12, the interference of the tapered shaft portion 24*k* of the plunger member 24*k* and the inside diameter 34*k* of the insertion member gripper end 16 to hold the plunger member 24*k* and the insertion member 12 together.

Figure 10:
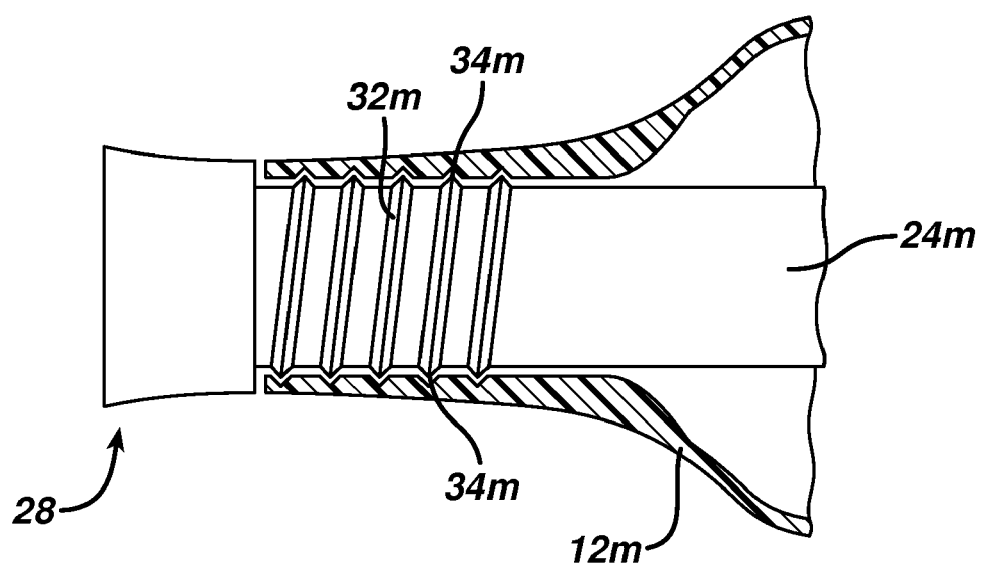
FIG. 10 is a partially cut away longitudinal section of an alternative embodiment of the present invention.

A screw thread system is shown in FIG. 10. The plunger member 24*m* and the insertion member 12*m* have screw threads 32*m*,34*m*. Screwing the two members 12*m*,24*m* together holds the plunger member 24*m* and the insertion member 12*m* together.

Figure 11:
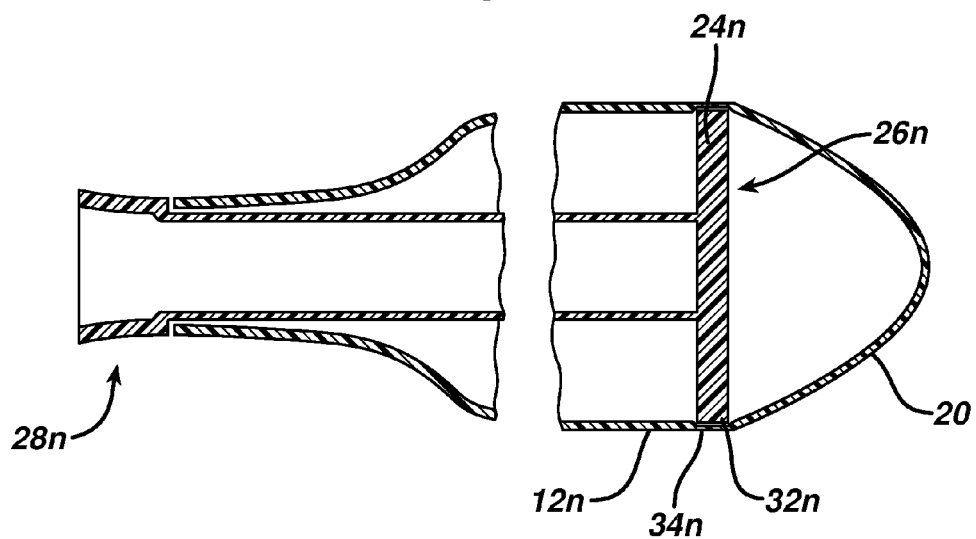
FIGS. 11 and 12 are partial longitudinal sections of the insertion and gripper ends of alternative embodiments of the present invention.

Insertion end interlocking systems (FIGS. 11 and 12):

In one embodiment, the plunger member 24*n* has enlarged diameters at the insertion end 26*n* and gripper end 28*n*. When the plunger member 24*n* is fully inserted into the insertion member 12, the enlarged insertion end flange 32*n* can fit into a recess 34*n* at the base of the insertion member petals 20.

Figure 12:
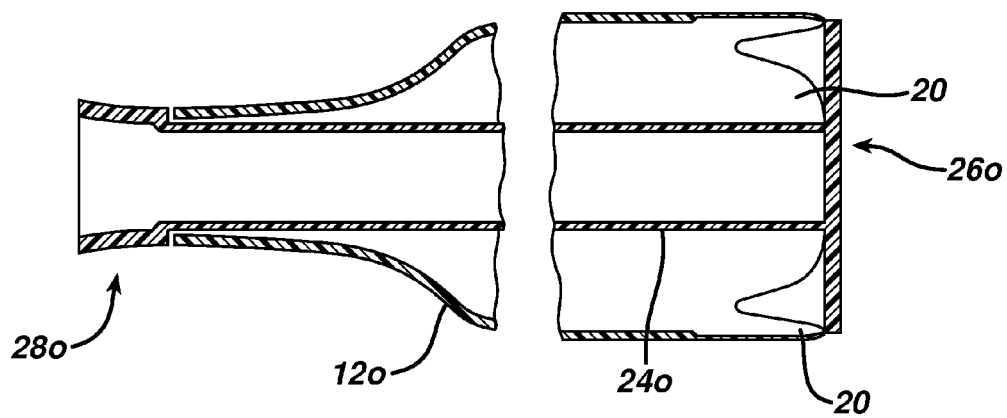

In an alternate embodiment shown in FIG. 12, the plunger member 24*o* again has enlarged diameters at the insertion end 26*o* and gripper end 28*o*. The plunger member 24*o* of this embodiment may be longer than the plunger member 24*n* of the previous embodiment to allow the enlarged insertion end flange 32*o* to extend beyond the insertion member petals 20 when the plunger member 24*o* is fully inserted into the insertion member 12. Once the enlarged plunger insertion end 26*o* extends beyond the petals 20, the petals 20 can revert towards their original, rounded position to hold the plunger member 24*o* and the insertion member 12 together.

Figure 13:
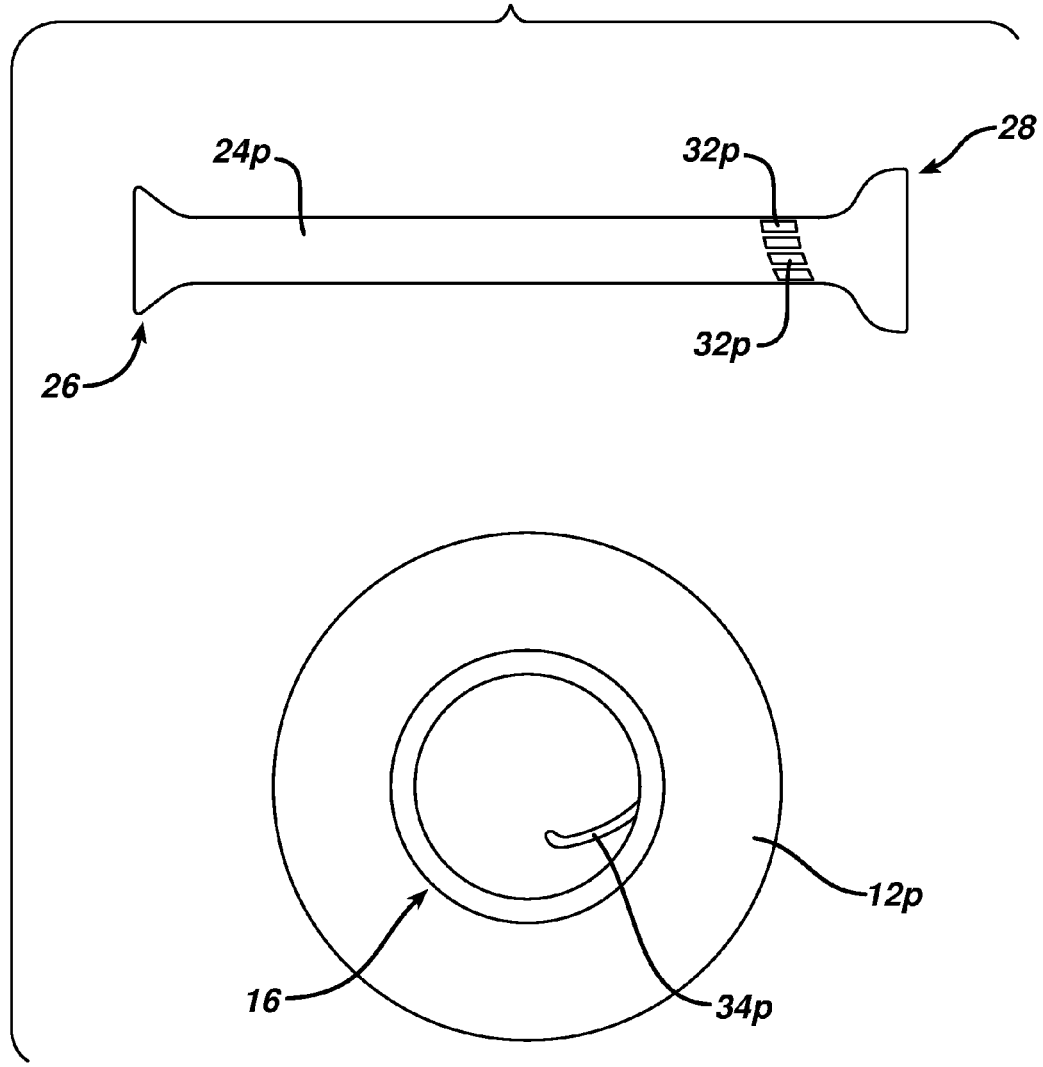
FIGS. 13A-B and 14A-B include a side elevation of alternative plunger members of the present invention and a gripper end view of alternative insertion members of the present invention.

Articulating detent systems:

In one embodiment shown in FIG. 13, the plunger member 24*p* is provided with a plurality of apertures 32*p* arranged proximate its gripper end 28. These apertures 32*p* may be arranged in a variety of patterns, and in one particular embodiment, they are arranged along a helical path on the plunger member tube. The insertion member 12*p* has at least one flexible detent 34*p* that extends toward the longitudinal axis of the insertion member 12*p* and toward its insertion end 14. As the plunger member 24*p* is pushed into the insertion member 12*p*, the flexible detent(s) 34*p* are deflected. If a removal force is applied to the plunger member 24*p*, the flexible detent(s) 34*p* are arranged and configured to extend into at least one aperture 32*p* to prevent withdrawal of the plunger member 24*p*.

Figure 14:
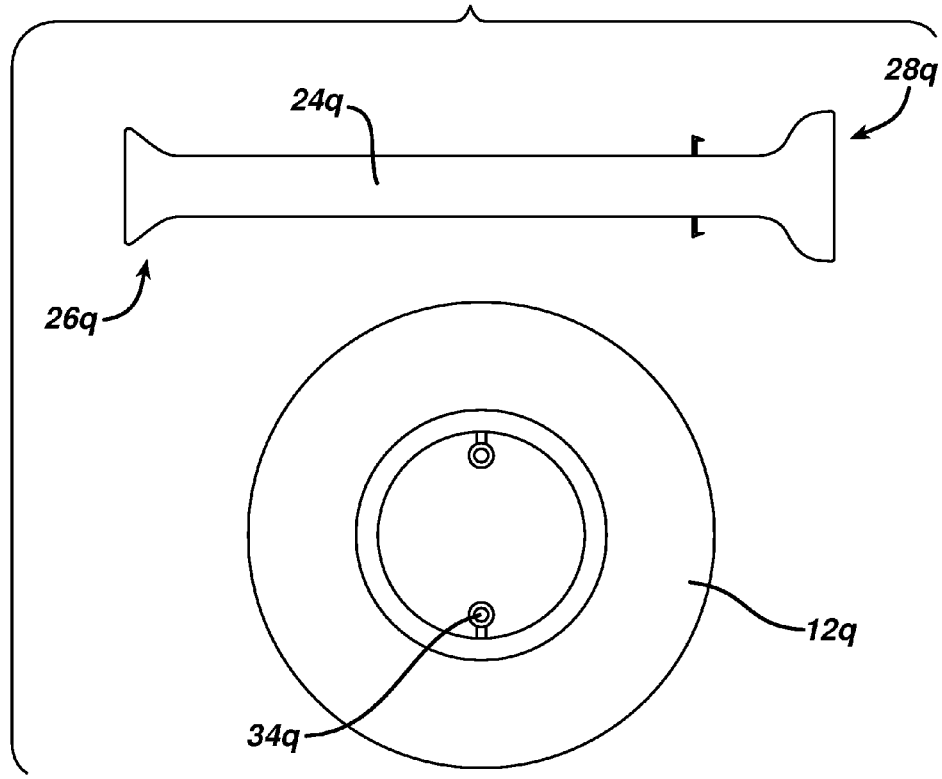

Hook and Loop (FIG. 14)—The plunger member 24*q* has a barbed hook 32*q* on the outer surface near its gripper end 28, and the insertion member 12*q* has matching open ring loops 34*q*. When the plunger member 24*q* is pushed into the insertion member 12*q* the hook 32*q* moves past a loop 34*q*. If the plunger member 24*q* is pulled out the hook(s) 32*q* catch on the loop(s) 43*q* to prevent withdrawal of the plunger member 24*q*.

Figure 15:
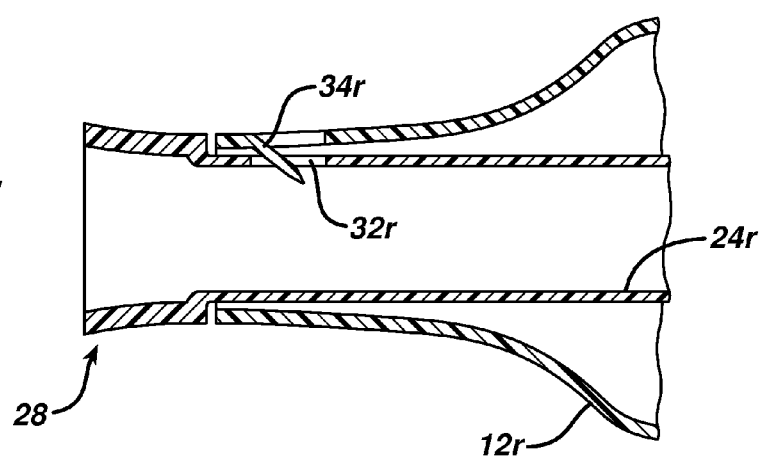
FIGS. 15 and 16 are partial longitudinal sections of alternative embodiments of the present invention.

Barrel Tang (FIG. 15)—The plunger member 24*r* has at least one slot 32*r* near its gripper end 28. The insertion member 12*r* has at least one tang 34*r* that is biased toward the longitudinal axis of the insertion member 12*r* and toward the insertion end 14. When assembled the unslotted portion of the plunger member 24*r* bears against the at least one tang 34*r*. However, when the plunger member 24*r* is used to expel the insertable device 18 and is fully inserted into the insertion member 12*r*, the at least one tang 34*r* aligns with the at least one slot 32*r* to permit it to deploy into the at least slot 32*r*. This holds the plunger member 24*r* and the insertion member 12*r* together.

Figure 16:
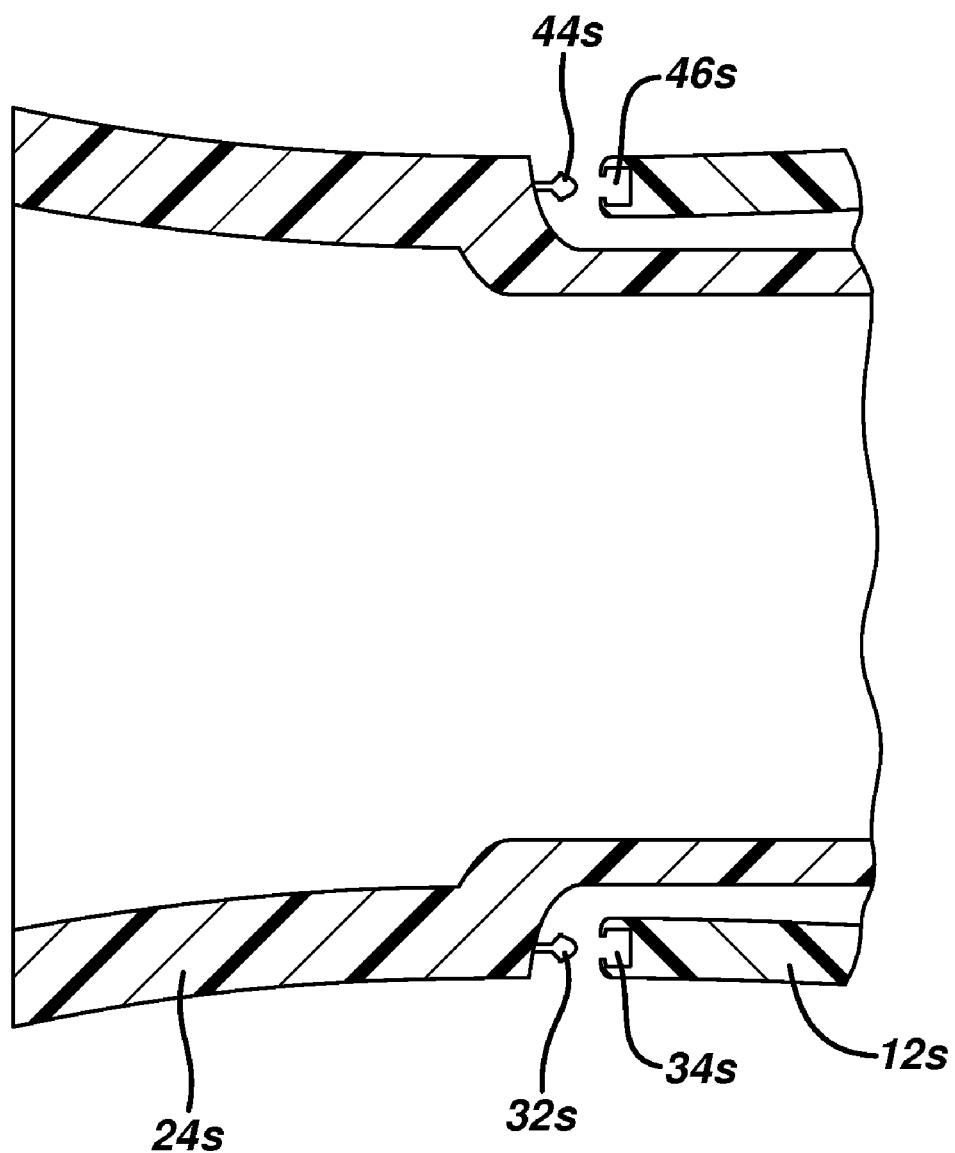

Another embodiment employs a detent and receiving aperture (FIG. 16). At least one detent 32*s* extends from the plunger member gripper end 28, generally parallel to the longitudinal axis of the plunger member 24*s*. The at least one detent 32*s* has an enlarged transverse dimension 44*s* distal its attachment to the plunger member gripper end 28. At least one aperture 34*s* at the insertion member gripper end 16 is aligned with the at least one detent 32*s* and has a transverse dimension 46*s* arranged and configured to cooperate with the at least one detent 32*s* during complete insertion of the plunger member 24*s* into the insertion member 12*s*. The at least one detent 32*s* and aperture 34*s* deform to allow the permit the enlarged transverse dimension 44*s* to fully enter the at least one aperture 34*s* to hold the plunger member 24*s* and the insertion member 12*s* together.

Figure 17:
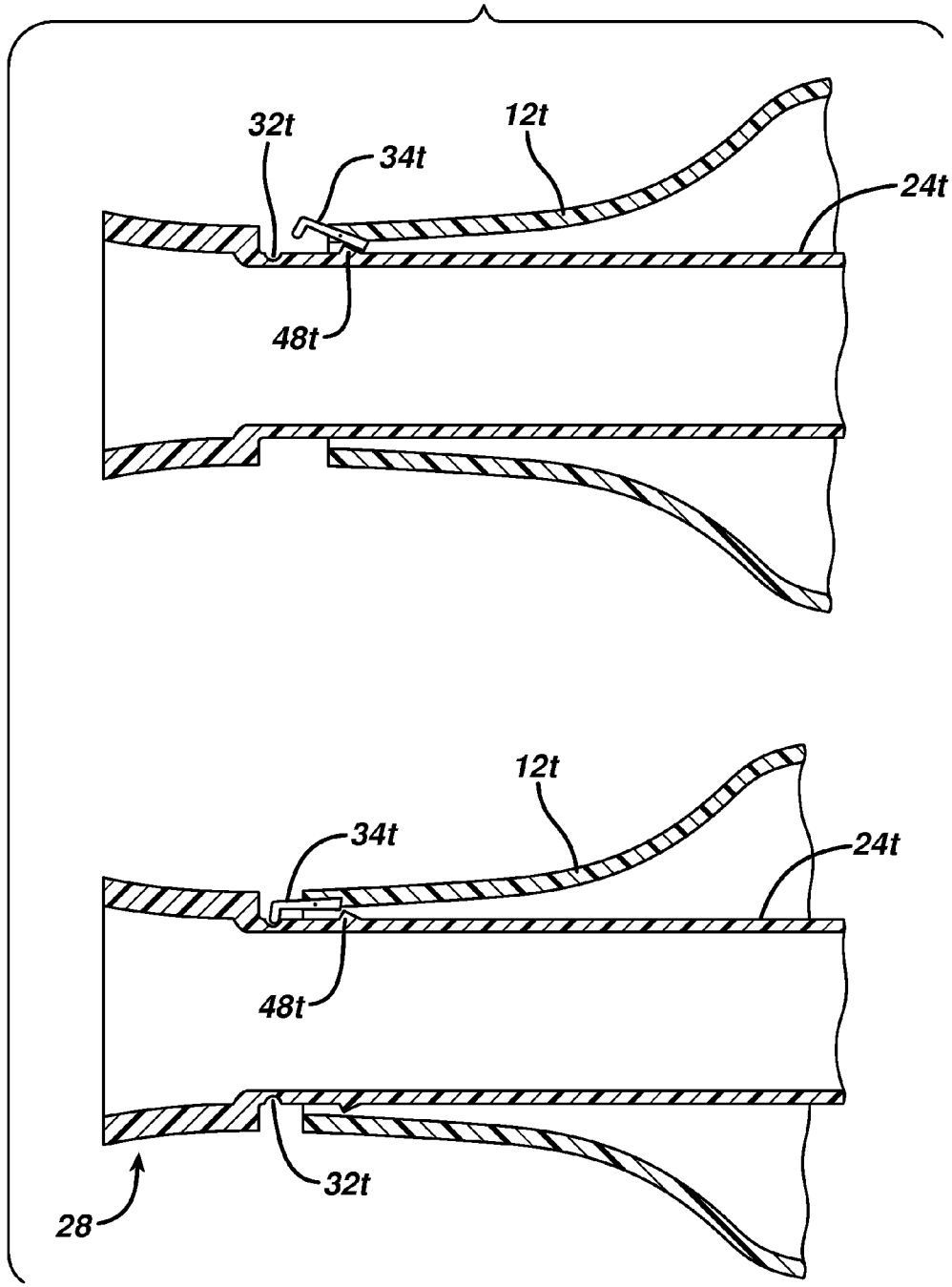
FIGS. 17A-B shows partial longitudinal sections of two stages of insertion of a plunger member into an insertion member according to an alternative embodiment of the present invention.

Toggle (FIG. 17)—The insertion member 12*t* has a hinged toggle 34*t* that pivots into a detent or depression 32*t* in the plunger member 24*t*. A raised portion 48*t* is spaced from the detent 32*t* toward the plunger member insertion end 26 when the plunger member 24*t* fully inserted into the insertion member 12*t* to hold the plunger member 24*t* in place.

Figure 18A:
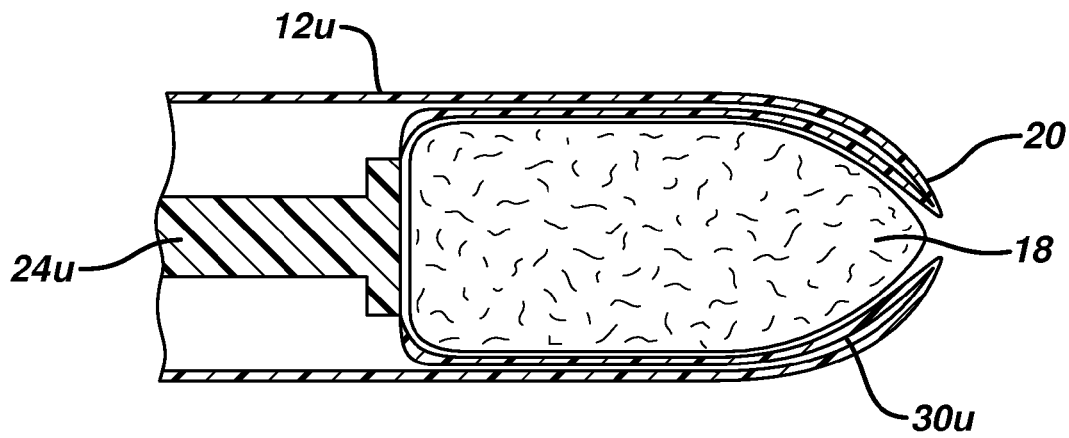
FIGS. 18A-18C show partial longitudinal sections of three stages of insertion of a plunger member into an insertion member according to an alternative embodiment of the present invention.
Figure 18B:
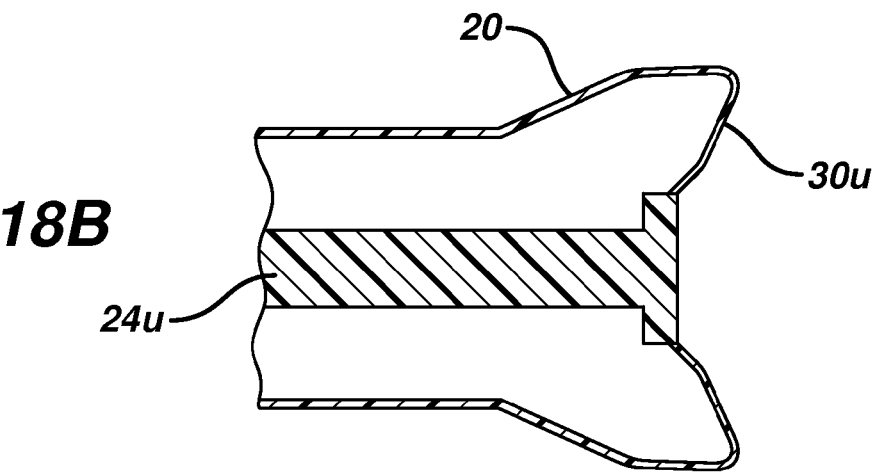
Figure 18C:
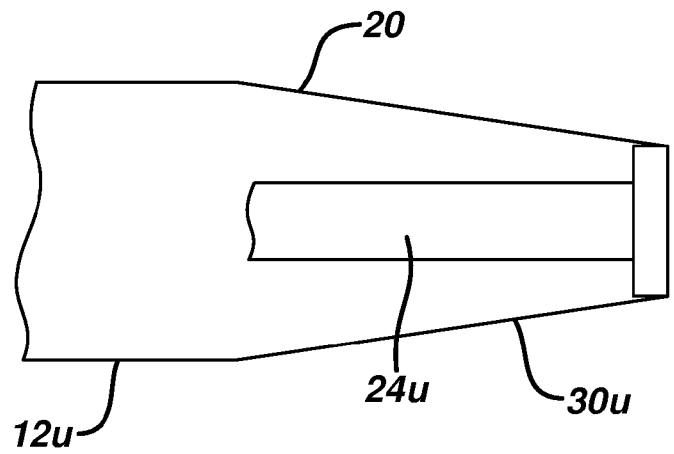

One piece (FIG. 18)—The insertion member 12*u* and the plunger member 24*u* can be molded together, joined by a thin section 30*u* as shown in FIG. 18A. As the plunger member 24*u* is inserted into the insertion member 12*u*, the thin section 30*u* stretches and then folds over on itself as shown in FIG. 18B. When the plunger member 24*u* is fully inserted into the insertion member 12*u*, the stretched thin section 30*u* straightens and regains a reduced diameter, as shown in FIG. 18C. This holds the insertion member 12*u* and the plunger member 24*u* together.

In use, the plunger member 24 is arranged and configured for slidable movement within the insertion member 12. The locking mechanism 30 includes at least one plunger lock element 32 and at least one insertion member lock element 34. When the plunger and insertion member locking elements 32,34 engage, the user may feel the engagement or at least recognize the full engagement of the members 12,24 by resistance to further movement. This permits a user to determine when the insertable device 18 is fully expelled. The locking mechanism 30 also holds the plunger member 24 fully inside the insertion member 12 to prevent their separation during removal of the applicator 10 from the user's body. While specific tube geometry is not critical, in order for the locking mechanism 30 to prevent separation of the insertion member 12 and plunger member 24, a locking mechanism 30 provided at least on a part of the insertion member 12 can be created.

Again, the insertion member 12 is sized and configured to house an insertable element, such as an absorbent tampon 18. The insertion member 12 should have a substantially smooth exterior surface that will facilitate insertion of the insertion member 12 into e.g. a woman's vagina. When the exterior surface is smooth and/or slippery, the insertion member 12 will easily slide into a woman's vagina without subjecting the internal tissues of the vagina to abrasion. The insertion member 12 can be coated to give it a high slip characteristic. Wax, polyethylene, a combination of wax and polyethylene, cellophane, clay, mica and other lubricants are representative coatings that can be applied to the insertion member 12 to facilitate comfortable insertion.

The applicator of the present invention may be formed by first providing an insertion member 12 having an insertion end 14 and a gripper end 16. Next, a plunger member 24 is provided having an insertion end 26 and a gripper end 28. A radial extending protrusion 32 may be formed proximate the plunger member gripper end 28. In some embodiments, the protrusion 32 may be formed proximate the plunger member insertion end 26

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. An applicator device capable of housing an insertable element comprising:
   a. an insertion member having a cylindrical central portion, an insertion end and an opposed gripper end having a smaller outer diameter than the cylindrical central portion of the insertion member,
   b. a plunger insertable into the smaller diameter of the gripper end of the insertion member and having an insertion end and an opposed gripper end, and
   c. a locking mechanism comprising at least one plunger lock element and at least one insertion member lock element;

wherein (1) the plunger is slidable in the insertion member between a second position, substantially withdrawn from the insertion member and a first position, substantially contained within the insertion member with the plunger insertion end disposed toward the insertion member insertion end to expel the insertable element contained within the insertion member; (2) the at least one plunger lock element and the at least one insertion member lock element are arranged and configured to engage when the plunger is disposed in the first position after expulsion of the insertable member; (3) at least one lock element has a taper lead; (4) the outer diameter of the gripper end of the plunger decreases in a direction towards the insertion end to create a sloped surface, the outer diameter of the gripper end of the tubular insertion member decreases in a direction away from the insertion end to create a sloped outer surface such that the outer diameter of the applicator device is substantially continuous where the gripper end of the plunger abuts the gripper end of the tubular insertion member; and (5) whereby the outer diameter of the plunger decreases to create a shoulder on the outer surface of the plunger such that the gripper end of the tubular insertion member is flush against the shoulder of the plunger.

2. The applicator device of claim 1, wherein the at least one plunger lock element is disposed proximate the gripper end of the plunger, and the at least one insertion member lock element is disposed proximate the gripper end of the insertion member.

3. The applicator device of claim 1, wherein the at least one insertion member lock element is located on an interior surface of the insertion member.

4. The applicator device of claim 1, wherein the at least one plunger lock element comprises a raised element.

5. The applicator device of claim 4, wherein the raised element comprises a radial protrusion.

6. The applicator device of claim 1, wherein the at least one insertion member lock element comprises a raised element.

7. The applicator device of claim 6, wherein the raised element comprises a radial ledge.

8. A method of inserting an element into a body cavity comprising the steps of:
   a. inserting an applicator into the body cavity, the applicator comprising:
      i. an insertion member having a cylindrical central portion, an insertion end and an opposed gripper end having a smaller outer diameter than the cylindrical central portion of the insertion member;
      ii. a plunger insertable into the smaller diameter of the gripper end of the insertion member and having an insertion end and an opposed gripper end; and
      iii. a locking mechanism comprising at least one plunger lock element and at least one insertion member lock element;
   wherein the plunger is slidable in the insertion member between a second position, substantially withdrawn from the insertion member and a first position, substantially contained within the insertion member with the plunger insertion end disposed toward the insertion member insertion end to expel the insertable element contained within the insertion member; the outer diameter of the gripper end of the plunger decreases in a direction towards the insertion end to create a sloped surface, the outer diameter of the gripper end of the tubular insertion member decreases in a direction away from the insertion end to create a sloped outer surface such that the outer diameter of the applicator device is substantially continuous where the gripper end of the plunger abuts the gripper end of the tubular insertion member; and whereby the outer diameter of the plunger decreases to create a shoulder on the outer surface of the plunger such that the gripper end of the tubular insertion member is flush against the shoulder of the plunger;
   b. sliding the plunger of the applicator into the insertion member to cause the at least one plunger lock element to engage the at least one insertion member lock element;
   c. expelling an insertable device from the insertion end of the applicator and into the body cavity; and
   d. withdrawing the applicator from the body cavity by withdrawing its plunger;
   wherein at least one lock element has a taper lead.

9. The method of claim 8, further comprising detecting the engagement of the at least one plunger lock element and the at least one insertion member lock element thereby signaling to the user the appropriate deployment of the insertable device in the body cavity.

10. The method of claim 8, wherein the at least one plunger lock element and the at least one insertion member lock element remain engaged during the withdrawal of the plunger.

* * * * *